(12) United States Patent
Hendricks et al.

(10) Patent No.: US 11,565,111 B2
(45) Date of Patent: Jan. 31, 2023

(54) SYSTEMS AND METHODS FOR TREATMENT OF CANCER USING ALTERNATING ELECTRIC FIELD GENERATION

(71) Applicant: Dignity Health, San Francisco, CA (US)

(72) Inventors: Benjamin Hendricks, San Francisco, CA (US); Kris Smith, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 193 days.

(21) Appl. No.: 17/260,019

(22) PCT Filed: Jul. 17, 2019

(86) PCT No.: PCT/US2019/042197
§ 371 (c)(1),
(2) Date: Jan. 13, 2021

(87) PCT Pub. No.: WO2020/018662
PCT Pub. Date: Jan. 23, 2020

(65) Prior Publication Data
US 2021/0308455 A1    Oct. 7, 2021

Related U.S. Application Data

(60) Provisional application No. 62/699,146, filed on Jul. 17, 2018.

(51) Int. Cl.
*A61N 1/36* (2006.01)
*A61N 1/05* (2006.01)
*A61N 1/372* (2006.01)
*A61N 1/40* (2006.01)

(52) U.S. Cl.
CPC ......... *A61N 1/3606* (2013.01); *A61N 1/0531* (2013.01); *A61N 1/0534* (2013.01); *A61N 1/36139* (2013.01); *A61N 1/37211* (2013.01); *A61N 1/37235* (2013.01); *A61N 1/40* (2013.01)

(58) Field of Classification Search
None
See application file for complete search history.

(56) References Cited

U.S. PATENT DOCUMENTS

| | | | |
|---|---|---|---|
| 2008/0046023 A1* | 2/2008 | Fischell | A61N 1/36185 607/45 |
| 2012/0203307 A1 | 8/2012 | Schroeppel | |
| 2017/0120041 A1 | 5/2017 | Wenger | |
| 2018/0289954 A1* | 10/2018 | Hebb | A61N 1/327 |

FOREIGN PATENT DOCUMENTS

| | | |
|---|---|---|
| WO | 2016179712 A1 | 11/2016 |
| WO | 2018057953 A2 | 3/2018 |

OTHER PUBLICATIONS

Extended European Search Report issued in corresponding Application 19837750.9 dated Mar. 18, 2022, 6 pages.

\* cited by examiner

*Primary Examiner* — Michael W Kahelin
(74) *Attorney, Agent, or Firm* — Polsinelli PC

(57) ABSTRACT

Various embodiments of a system and method for the treatment of brain cancer using a subdurally-implanted alternating electric field generation apparatus are disclosed herein.

20 Claims, 4 Drawing Sheets

SYSTEMS AND METHODS FOR TREATMENT OF CANCER USING ALTERNATING ELECTRIC FIELD GENERATION

CROSS REFERENCE TO RELATED APPLICATIONS

This is a PCT application that claims benefit from U.S. provisional application Ser. No. 62/699,146 filed on Jul. 17, 2018, which is incorporated by reference in its entirety.

FIELD

The present disclosure generally relates to the treatment of cancer, and in particular to treatment of brain cancer via electric field generation.

BACKGROUND

Alternating electric field (AEF) therapy, is a type of electromagnetic field therapy which uses low-intensity electrical fields to treat brain cancer tumors; glioblastoma in particular. Conventional cancer treatments include chemotherapy and radiation, which are associated with treatment-related toxicity and high rates of tumor recurrence. AEF uses an alternating electric field to disrupt cell division in cancer cells, thereby inhibiting cellular replication and initiating apoptosis (cell death). However, some topical AEF treatment methodologies are associated with skin irritation and rashes, as well as a requirement of the patient to maintain a shaved head and restrict physical activity.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Figure 1:
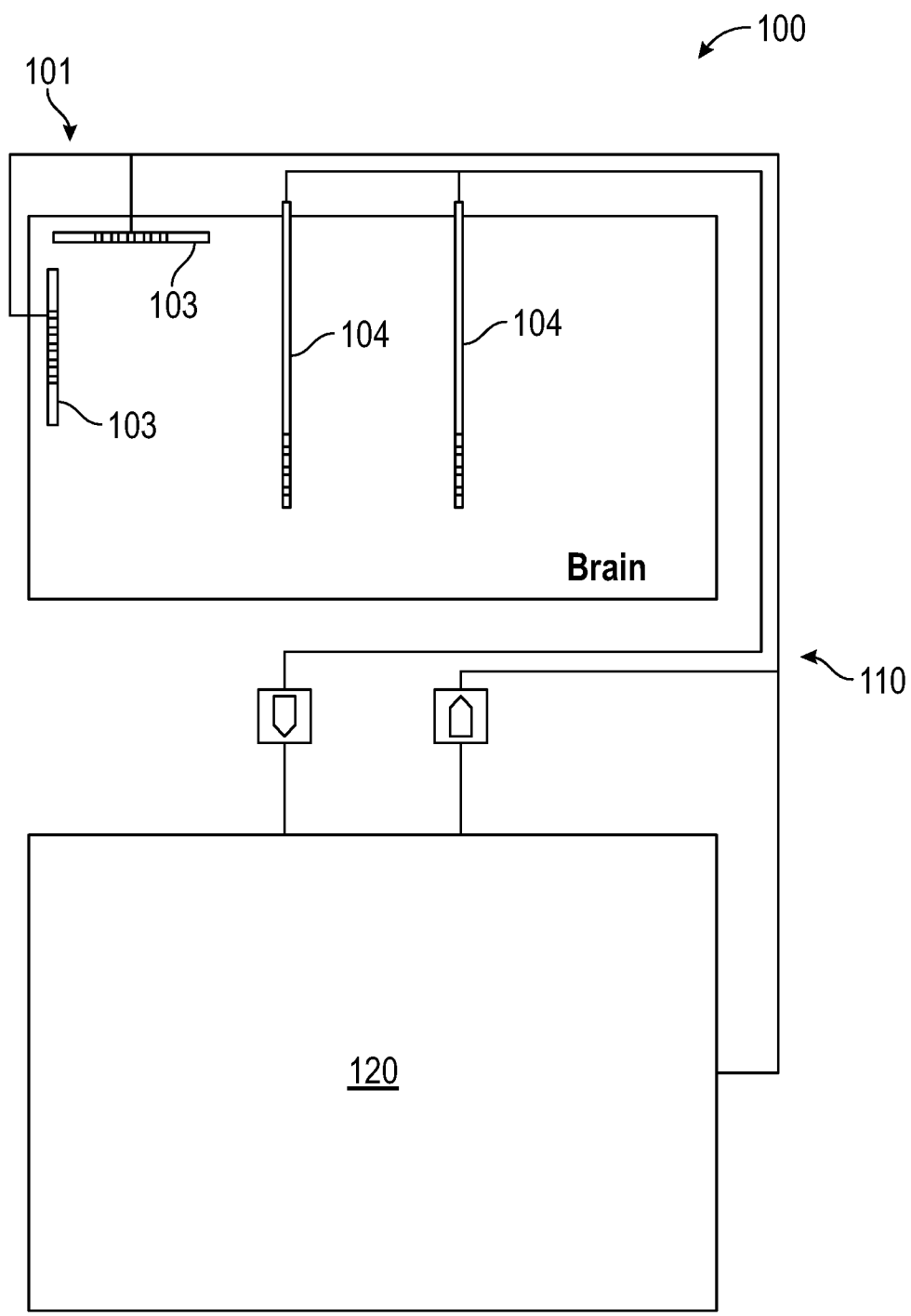
FIG. 1 is a diagram showing an electrode array and controller module of the present system with the electrode array implanted into a brain and the controller module with wires operatively connected to the electrode array.

Alternating electric field application is a burgeoning cancer treatment type with the potential to reduce treatment related toxicity. In alternating electric field application, an alternating electric field is applied to a cancerous region of the brain, thereby disrupting cellular division for rapidly-dividing cancer cells. To administer alternating electric field treatment to a patient, a system and method for an alternating electric field generation apparatus, herein referred to as "the present system", for generating an alternating electric field of optimized strength at a desired location within a body to inhibit cellular division and/or initiate apoptosis of cancer cells at the targeted treatment location is disclosed herein.

The present system provides, among other aspects, a system and method of a subdural implant apparatus wherein, through the use of an array of subdural electrodes implanted subdurally and deep-stimulating electrodes implanted deep into the brain tissue, a targeted alternating electric field is generated for the treatment of rapidly dividing cancer cells. In one aspect, the array of stimulating electrodes is in operative communication with a controller module, wherein the controller module produces a waveform to create the alternating electric field and receives feedback from the array of stimulating electrodes. Referring to the drawings, embodiments of the present system are generally indicated as 100 in FIGS. 1-5.

Figure 2:
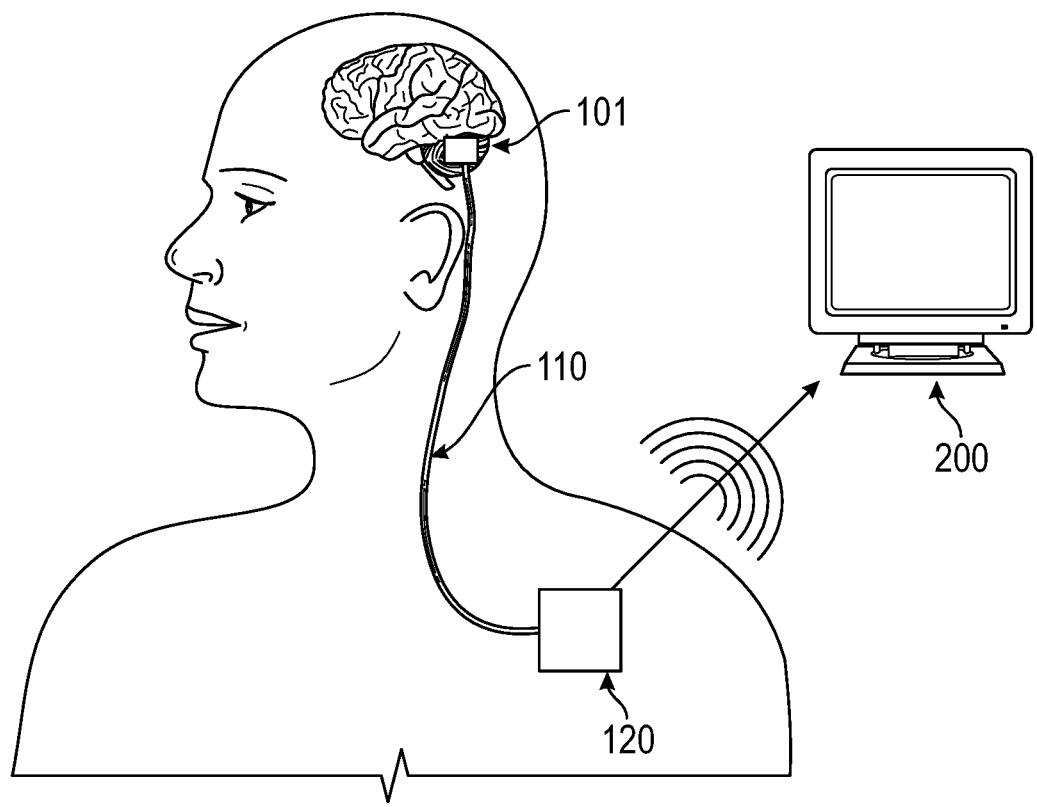
FIG. 2 is an illustration of the system of FIG. 1 relative to the body of a patient.

Referring to FIGS. 1 and 2, in some embodiments of the present system 100, a main array 101 including stimulating electrodes 103 and 104 is configured to be placed underneath the dura mater of a patient's brain. The main array 101 is in operative communication with a controller module 120 by way of a wire array 110. The controller module 120 is operable to generate an alternating electric field, receive feedback from the main array 101, and communicate with an external computer 200 for receiving operating parameters as well as exporting operating data related to the strength of the alternating electric field.

The main array 101 may include a plurality of subdural electrodes 103 as well as a plurality of deep-stimulating electrodes 104, such that the subdural electrodes 103 and deep-stimulating electrodes 104 are operable to generate an alternating electric field that is applied to brain tissue. In one aspect, the alternating electric field is configured for appropriate strength and distribution such that cancerous cells in contact with the alternating electric field are prevented from dividing. In some embodiments, one or more wires 102, each defining a respective distal end, extend from a respective subdural electrode 103 and terminates in a conductive contact. In one possible application, each of the plurality of subdural electrodes 103 are placed on the surface of the brain. In some embodiments, the subdural electrodes 103 may be thin enough to fit between the dura mater and the brain of the patient and may in some embodiments be surrounded by gel. Each subdural electrode 103 defines a proximal face 105 and a distal face (not shown), wherein the proximal face is in operative association with a distal end of each wire 102 and the distal face includes a transducing contact that is applied to the exterior of the brain. In some embodiments, the deep-stimulating electrodes 104 have elongated rod-shaped members comprising segmented strips of conductive material. The deep-stimulating electrodes 104 are implanted deep into the brain to facilitate penetration of the alternating electric field into the brain tissue. In some embodiments each of the deep-stimulating electrodes 104 defines a distal end and a proximal end, wherein the distal end of each of the deep-stimulating electrodes 104 is implanted into the brain tissue and the proximal end of each of the deep-stimulating electrodes 104 is in operative association with a respective wire 102. In some embodiments, the deep-stimulating electrodes 104 are operable to measure aspects of the alternating electric field applied to various locations within the brain by the main array 101 and communicate measured aspects of the alternating electric field back to the controller module 120. In one aspect, each subdural electrode 103 and deep-stimulating electrode 104 is operable to apply to tissue a current waveform through the wires 102. An alternating electric field is generated by the application of the waveform to the brain from multiple sources.

Figure 3:
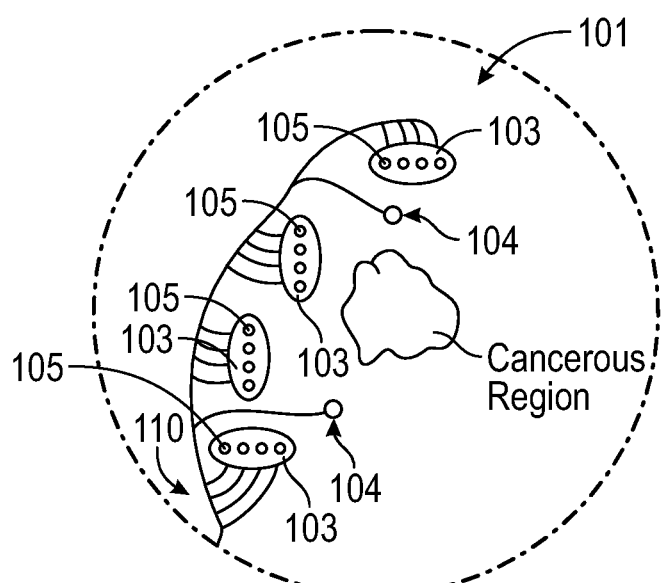
FIG. 3 is an illustration showing how the arrangement of the electrode array of the system of FIG. 1 may surround a cancerous region of the brain.

One visual example of the placement of subdural electrodes 103 and deep-stimulating electrodes 104 relative to a cancerous region of the brain is shown in FIG. 3. The optimal placement and number of subdural electrodes 103 and deep-stimulating electrodes 104 may vary between patients. Thus, a variety of imaging platforms may be used to scan the brain and determine optimal placement, types, and quantity of electrodes 103 and 104 to collectively create the array 101.

Figure 4:
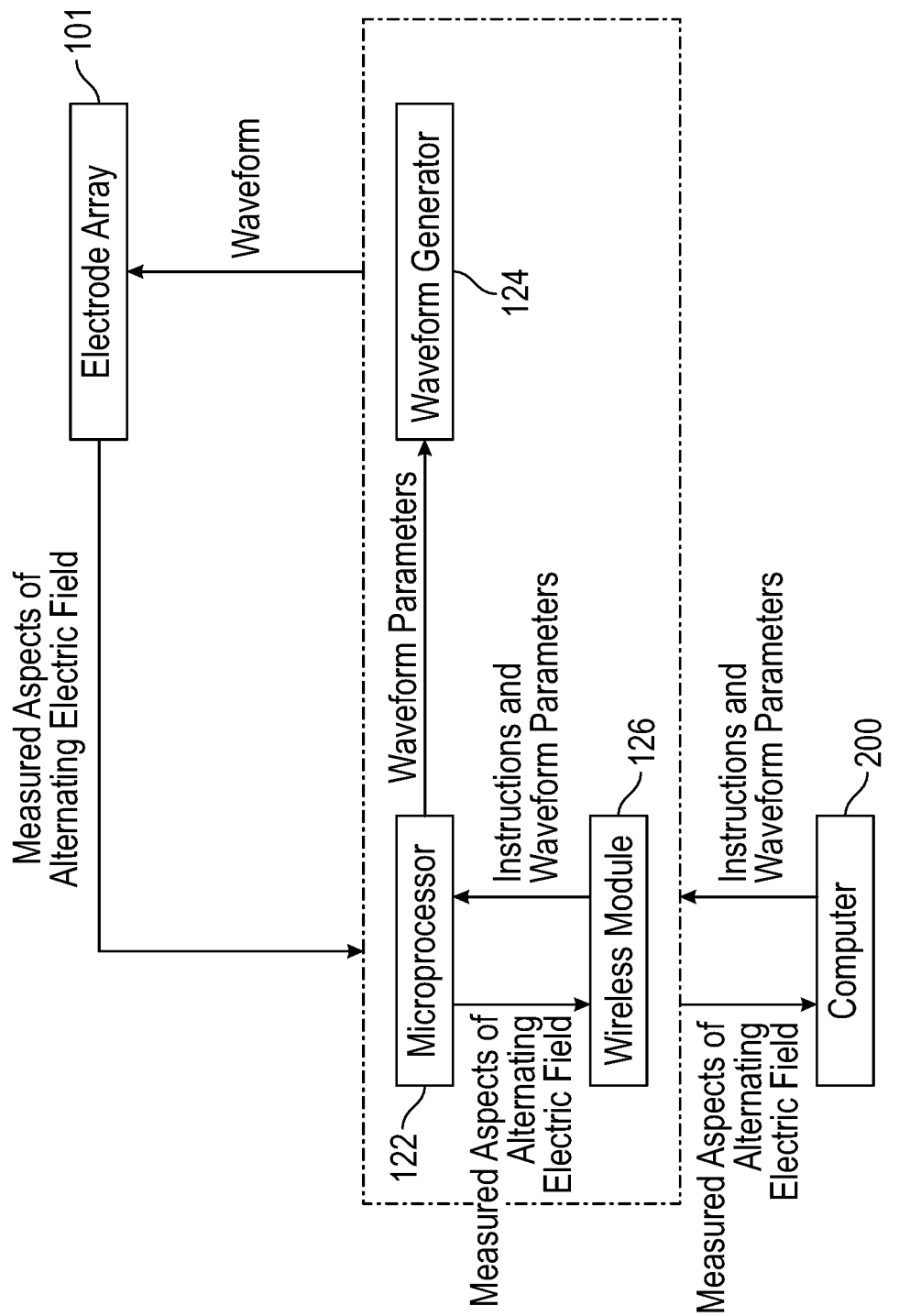
FIG. 4 is a simplified block diagram showing how the hardware of the controller module, the external computer, and the electrode array of the system of FIG. 1 interact.

Referring to FIG. 4, in some embodiments the controller module 120 includes a waveform generator 124 and a processing unit 122, wherein the waveform generator 124 is in operative communication with the array 101 by one or more wires 110. The waveform generator 124 of the controller module 120 is operable to receive a set of operating parameters from the processing unit 122 and output a waveform such that when the waveform is distributed throughout the array 101, an alternating electric field is applied to brain tissue. The processing unit 122 of the controller module 120, such as a microprocessor or a microcontroller, is operable to output the set of operating parameters for the waveform generator 124. The processing unit 122 is also operable to receive input from the array 101 pertaining to measured aspects of the alternating electric field and communicate the input to an external computer 200, update the set of operating parameters, and communicate the updated set of operating parameters to the waveform generator 124.

Empirical research for TTF therapy recommends a 200 kHz standard waveform to be produced by the waveform generator 124 to generate the alternating electric field. Ideal waveform modulation and intensity parameters are determined by the external computer 200 and delivered to the waveform generator 124 through the processing unit 122.

The controller module 120 may also include a wireless communication module 126 that allows communication between the processing unit 122 of the controller module 120 and external computer 200. In this manner, the processing unit 122 of the controller module 120 is operable to wirelessly receive software updates and instructions from the external computer 200 as well as transmit the measured aspects of the alternating electric field to the external computer 200 for review and system optimization. The controller module 120 may also include an implantable battery (not shown) or other power supply.

Figure 5:
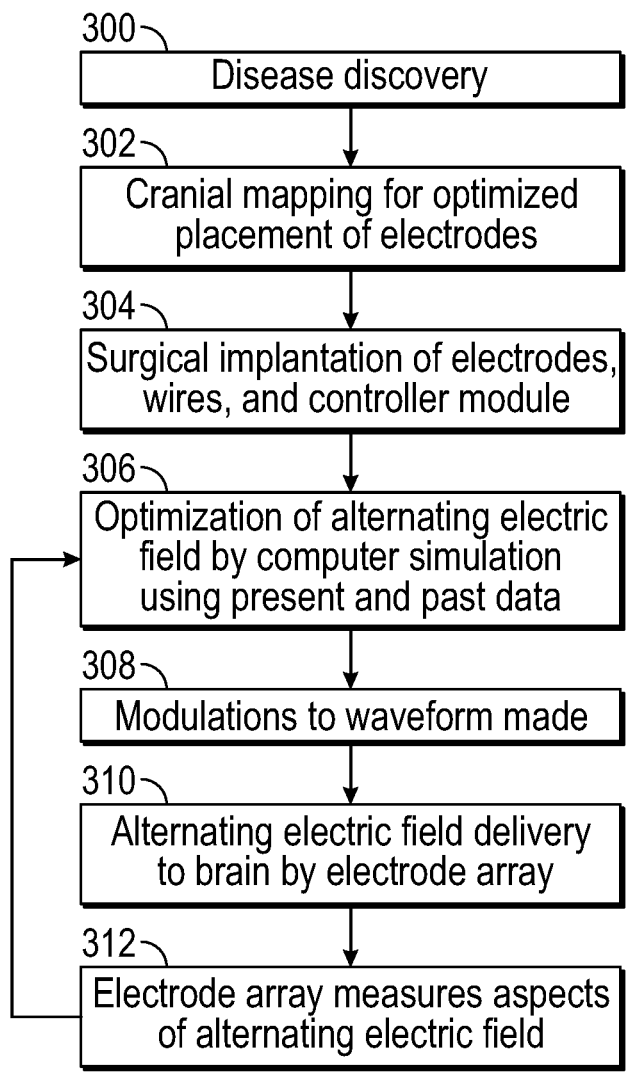
FIG. 5 is a flowchart showing the process of treatment and optimization for a patient using the system of FIG. 1.

A method for the treatment of cancer using the system 100 is illustrated in FIG. 5. At step 300 the disease is discovered and at step 302, one or more cranial mapping techniques are employed to determine optimal placement and arrangement for the electrode array 101. At step 304, the electrode array 101, wires 110, and controller module 120 are surgically attached or implanted. Referring back to FIG. 2, the electrode array 101 is implanted in the cranium of a patient, wherein the subdural electrodes 103 are placed subdurally on the surface of the brain and the deep-stimulating electrodes 104 are implanted deep into the brain. The controller module 120 may be surgically implanted or installed subclavically or in the abdomen. In other cases, the controller module 120 may be installed outside the body, depending on the anatomy of the patient.

Referring back to FIG. 5, once the electrode array 101, wires 102, and control module 120 are attached or implanted, at step 306 the alternating electric field generated by the electrode array 101 is optimized using an initial set of parameters and the known location of each subdural electrode 103 and deep-stimulating electrode 104 on or within the patient's brain. The optimization process is performed using an external computer 200 that executes a simulation environment application to determine optimal waveform operating parameters for the controller module 120. The simulation environment application may be embodied as a program or an application and may be installed and operated on the external computer 200. When feedback information from the array 101 is available, the feedback is incorporated into the optimization step 306. At step 308, optimal waveform operating parameters are communicated to the controller module 120 and at step 310 the optimized alternating electric field is then applied to the brain of the patient by the array 101. As the alternating electric field is delivered, one or more of the deep stimulating electrodes 104 measure aspects of the alternating electric field and communicate this data to the controller module 120. The controller module 120 records and/or transmits the information to the external computer 200 at step 312. In this manner, the optimization process can be iteratively repeated using feedback pertaining to measured aspects of the alternating electric field and the exact location of each subdural electrode 103 and deep-stimulating electrode 104 until the alternating electric field is at its most effective application strength.

In some embodiments of the system 100, the simulation environment used in the optimization process using the external computer 200 is operable to obtain the exact positions of the subdural electrodes 103 and the deep-stimulating electrodes 104 as input as well as including information about the alternating electric field strength as measured by the deep-stimulating electrodes 104. In addition, the simulation environment application is operable to allow the user to observe changes in the alternating electric field delivered to the brain by changes in the waveform delivered to any given electrode 103 or 104. As changes in the delivered waveform are simulated, the simulation environment application is operable to optimize the alternating electric field generation by calculating and displaying a distribution of alternating electric field strength throughout the brain as a result of the changes in the delivered waveform, the exact positions of the electrodes 103 and 104, and/or the unique anatomy of the patient's brain. This allows the user to determine the best configuration of electrode stimulation parameters for electrodes 103 and 104 to optimize the alternating electric field in the targeted region. A given parameter may then be initialized in the patient and altered while real-time data is acquired by one or more of the deep-stimulating electrodes 104 in the brain to ensure adequate alternating electric field strength is achieved.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system for the treatment of brain cancer, comprising:
   an alternating electric field generation apparatus, comprising:
      an electrode array, comprising:
         an electrode array comprising a plurality of subdural electrodes, wherein each of the subdural electrodes is implantable subdurally onto the brain of a patient;

a plurality of deep-stimulating electrodes, wherein each of the plurality of deep-stimulating electrodes is implantable within the brain of the patient;

wherein the electrode array delivers an alternating electric field to the tissue of the brain through the plurality of subdural electrodes and the plurality of deep-stimulating electrodes; and a controller module in operative communication with the electrode array, wherein the controller module is operable to generate a waveform representative of the alternating electric field, and configured for the treatment of brain cancer wherein the waveform is transmitted to the electrode array; and an external computer, wherein the external computer is operable to receive feedback from the controller module and wherein the external computer is operable to send commands to the controller module;

wherein the controller module is operable to incorporate feedback from the electrode array and communicate the feedback to the external computer.

2. The system of claim 1, wherein the controller module comprises a wireless module, wherein the wireless module is operable to communicate with the external computer wirelessly.

3. The system of claim 2, wherein the controller module further comprises a processing unit, wherein the processing unit is operable to receive data pertaining to electric field strength from the electrode array, wherein the processing unit is in operative communication with the wireless module.

4. The system of claim 1, further comprising:

a plurality of conductive wires, wherein one or more of the plurality of conductive wires are operable to transmit data pertaining to electric field strength from the electrode array to the controller module, and wherein one or more of the plurality of conductive wires are operable to transmit the waveform from the controller module to the electrode array.

5. The system of claim 1, wherein the external computer is operable to incorporate the feedback from the electrode array, a location of each of the plurality of subdural electrodes on the brain, and a location of each of the plurality of deep stimulating electrodes within the brain.

6. The system of claim 5, wherein the external computer is operable to simulate effects of a set of parameters pertaining to the waveform on the brain, wherein the waveform is representative of the alternating electric field.

7. An alternating electric field generation apparatus for the treatment of brain cancer, comprising:

an electrode array, comprising:

an electrode array comprising a plurality of subdural electrodes, wherein each of the plurality of subdural electrodes is implantable subdurally onto the brain of a patient; and a plurality of deep-stimulating electrodes, wherein each of the plurality of deep-stimulating electrodes is implantable within the brain of the patient; and wherein the electrode array delivers an alternating electric field to the tissue of the brain; and a controller module in operative communication with the electrode array, the controller module comprising:

a waveform generator, wherein the waveform generator is operable to generate a waveform representative of the alternating electric field, and configured for the treatment of brain cancer wherein the waveform is transmitted to the electrode array; and a processing unit, wherein the processing unit is operable to communicate a set of waveform parameters to the waveform generator; and wherein the waveform generator is operable to transmit a waveform to the electrode array by one or more wires.

8. The apparatus of claim 7, wherein the processor is operable to receive a set of measured aspects of the alternating electric field from one or more of the plurality of deep-stimulating electrodes of the electrode array.

9. The apparatus of claim 8, wherein one or more of the plurality of conductive wires are operable to transmit the set of measured aspects of the alternating electric field from the electrode array to the controller module.

10. The apparatus of claim 7, comprising a plurality of conductive wires, wherein one or more of the plurality of conductive wires are operable to transmit the waveform from the controller module to the electrode array.

11. The apparatus of claim 7, wherein each of the plurality of deep stimulating electrodes define a rod-shaped member and wherein one or more conductive contacts are disposed along the rod-shaped member, wherein a proximal end of each of the plurality of deep stimulating members is in operative association with one or more of the plurality of conductive wires.

12. The apparatus of claim 7, wherein each of the plurality or subdural electrodes define opposing faces, wherein a distal face of the opposing faces comprises a conductive contact and wherein a proximal face of the opposing faces is in operative association with one or more conductive wires.

13. A method for the treatment of cancer using an alternating electric field generation system, the method comprising:

implanting the alternating electric field generation system into a patient, wherein a plurality of subdural electrodes of the alternating electric field generation system are implanted subdurally onto the brain of a patient, and wherein a plurality of deep-stimulating electrodes of the alternating electric field generation system are implanted into the brain of the patient, wherein the alternating electric field generation system further comprises a controller module;

delivering an alternating electric field configured for the treatment of brain cancer to the brain using the plurality of subdural electrodes and the plurality of deep-stimulating electrodes, wherein the plurality of deep-stimulating electrodes are operable to measure aspects of the alternating electric field and communicate them to the controller module; and optimizing the alternating electric field generation system using the measured aspects of the alternating electric field and a set of locations representative of each of the subdural electrodes and each of the deep-stimulating electrodes, wherein a set of waveform parameters are transmitted to the controller module.

14. The method of claim 13, wherein the optimization of the alternating electric field generation system is performed by an external computer, wherein the external computer computes the set of waveform parameters for the alternating electric field generation system using a simulation environment application.

15. The method of claim 14, wherein the controller module is operable to send the measured aspects of the alternating electric field to the external computer, and wherein the external computer is operable to send the set of waveform parameters to the controller module.

16. The method of claim 13, further comprising:
determining an optimal placement configuration for each of the plurality of subdural electrodes and each of the plurality of deep-stimulating electrodes using cranial mapping software.

17. The method of claim 13, further comprising:
initializing the alternating electric field generation system, wherein a set of initial waveform parameters are sent to the controller module.

18. The method of claim 14, wherein the simulation environment application predicts changes in the alternating electric field corresponding to a change in a waveform transmitted to the plurality of subdural electrodes or deep-stimulating electrodes.

19. The method of claim 18, wherein the simulation environment application is operable to obtain a set of locations for each of the plurality of subdural electrodes or deep-stimulating electrodes and calculate a predicted distribution of the alternating electric field based on the waveform delivered to each of the plurality of subdural electrodes or deep-stimulating electrodes.

20. The method of claim 19, wherein the alternating electric field generation system is optimized by choosing the set of optimal waveform parameters which deliver an alternating electric field of appropriate distribution and strength to a cancerous region of the brain, wherein the set of optimal waveform parameters is representative of the waveform delivered to each of the plurality of subdural electrodes or deep-stimulating electrodes.

* * * * *